United States Patent [19]

Kulberg et al.

[11] 4,141,444
[45] Feb. 27, 1979

[54] CAM AND LEVER BASED SAMPLE TRANSPORT

[75] Inventors: Gerardus H. Kulberg, Noorden; Jakob Feiken, Nieuwveen; Siebe A. Freek, Zaandam, all of Netherlands

[73] Assignee: G. D. Searle & Co., Chicago, Ill.

[21] Appl. No.: 792,779

[22] Filed: May 2, 1977

[51] Int. Cl.² .............................................. B65G 35/08
[52] U.S. Cl. ................................. 198/472; 198/580; 198/740; 198/745; 198/795
[58] Field of Search .............. 198/472, 580, 648, 655, 198/740, 741, 744, 745, 793, 795; 214/310

[56] References Cited

U.S. PATENT DOCUMENTS

| | | | |
|---|---|---|---|
| 1,559,199 | 10/1925 | Straight | 198/472 |
| 3,272,240 | 9/1966 | Roth | 198/472 |
| 3,315,778 | 4/1967 | Kendall, Sr. et al. | 198/580 |
| 3,418,084 | 12/1968 | Allington | 198/472 |
| 3,451,564 | 6/1969 | Haas | 198/472 |
| 3,809,208 | 5/1974 | Shields | 198/580 |
| 3,844,428 | 10/1974 | Olsen | 198/472 |
| 3,951,605 | 4/1976 | Natelson | 198/472 |
| 3,966,038 | 6/1976 | Redmer et al. | 198/472 |
| 3,976,289 | 8/1976 | Baghuis | 198/793 |
| 4,040,533 | 8/1977 | De Boer et al. | 198/472 |

FOREIGN PATENT DOCUMENTS

| | | | |
|---|---|---|---|
| 922510 | 1/1955 | Fed. Rep. of Germany | 198/580 |
| 2529071 | 2/1976 | Fed. Rep. of Germany | 198/472 |

Primary Examiner—Robert B. Reeves
Assistant Examiner—Richard K. Thomson
Attorney, Agent, or Firm—Dennis O. Kraft

[57] ABSTRACT

A sample transport mechanism is disclosed for conveying test tube samples in an endless path to and then away from a test station. The samples are removably inserted into elongated test tube supports arrayed upon a table in two rows and moveable in a rectangular path. Underlying the table is a plate generally coextensive therewith and having brackets mounting pins projecting above the margin of the table above and below the rows. The sample supports have parallel grooves in their bottom surfaces transverse to the longitudinal axis of the supports, and into which the pins may engage. The plate also has two openings, one square and the other rectangular, and into which are engaged cams. The cams when rotated move the plate in a rectangular path with respect to the table. The spacing of the pin and slots is such that the pins normally engage two diagonally opposite corner trays and move them longitudinally toward the next row by the incremental distance separating two adjacent samples. When both such trays are moved completely to the next row, the pin-slot spacing is then such that the pins engage a non-slotted portion of the sample carriers, thereby moving them laterally and positioning subsequent sample carriers for incremental longitudinal movement to repeat the cycle.

16 Claims, 2 Drawing Figures

CAM AND LEVER BASED SAMPLE TRANSPORT

BACKGROUND OF THE INVENTION

This invention relates to transport mechanisms for moving test samples to and from a test station in systems for measurement and recording of sample properties, such as radioactivity, light transmissivity or fluorescene, or for sample preparation in diagnostic testing prior to such measurements. More particularly, it relates to test sample transport systems which depend upon levers as opposed to chains or conveyors to move the samples to test stations.

Conventional sample transport mechanisms for the above purposes, have been known and utilized for many years. The predominant characteristics of such transports have been the use of chains and sprockets in a serpentine configuration, or other endless chain-type conveyors in another configuration. These may be seen in applications either for carrying discrete samples, or for driving trays supporting a set number of samples in a predetermined path. The degree of complexity of such conventional sample transports, the consequent expense of both manufacture and maintenance, and the inherent reliability problem have long been recognized as disadvantages which it would be desirable to obviate.

It has been attempted to obviate these disadvantages through various modifications involving cams, levers and guides, but it has been found that no great degree of simiplification has actually been obtained. Rather, problems have been merely transferred to other areas of the mechanism. Moveover, it has been found that such prior designs have been primarily amenable to transport of either trays or discrete samples, but not both.

SUMMARY OF THE INVENTION

Accordingly, it is the principal object of the invention to provide a sample transport system of much greater simplicity, compactness and reduced number of moving parts.

It is another object of the invention to provide a sample transport system whose principal motive parts are levers and cams, and which requires only a single motor.

It is a still further object of the invention to provide a sample transport system amenable to use in a variety of sample preparation measurement and diagnostic test contexts.

It is yet another object of the invention to provide a sample transport system which is capable of applications involving both the transport of samples in trays, and the transport of discrete samples.

It is a still further object of the invention to provide a sample transport system of at least equivalent quality to prior systems, but of much lower inherent cost.

In a preferred embodiment, the invention is a transport mechanism for conveying samples to a test station, comprising a plurality of longitudinally elongated test tubes supports, each having a plurality of longitudinally evenly spaced receptacles accepting test samples and having defined therebelow a plurality of longitudinally spaced grooves perpendicular to the longitudinal direction, and bearing a regular relationship with the spacing between the receptacles, the supports having a limited portion near the ends thereof which is not grooved. The transport mechanism is a planar table mounting the supports in two side-by-side rows and permitting the supports to be moved in a rectangular path and longitudinally across at the ends of the rows into the opposite row. Also included is a plate generally coextensive with and immediately underlying the table, and moveable with respect thereto, the plate having marginally mounted pins held above the margin of the table and extending parallel to and in the plane of the grooves, at least one such pin being provided at the ends of each of the rows, the plate being provided with at least one generally rectangular opening, the dimensions of the opening being related to the spacing between the grooves and the width of the supports. Finally included is a cam engaging the aforementioned opening for rotation therewithin to move the plate in a generally rectangular path offset about the table, whereby the pins normally engage two sample supports positioned at the diagonally opposite ends of two of the rows, and move the two supports longitudinally across toward the opposite row by the incremental distance relating to the spacing between two adjacent receptacles. This movement is repeated in repetitive sequence until each of the two supports align with the opposite row, whereupon the pins engage and non-grooves portions of the supports. The pins then move the supports in the direction of the rows to position subsequent supports at these diagonally opposite ends to repeat the cycle.

DETAILED DESCRIPTION

Figure 2:
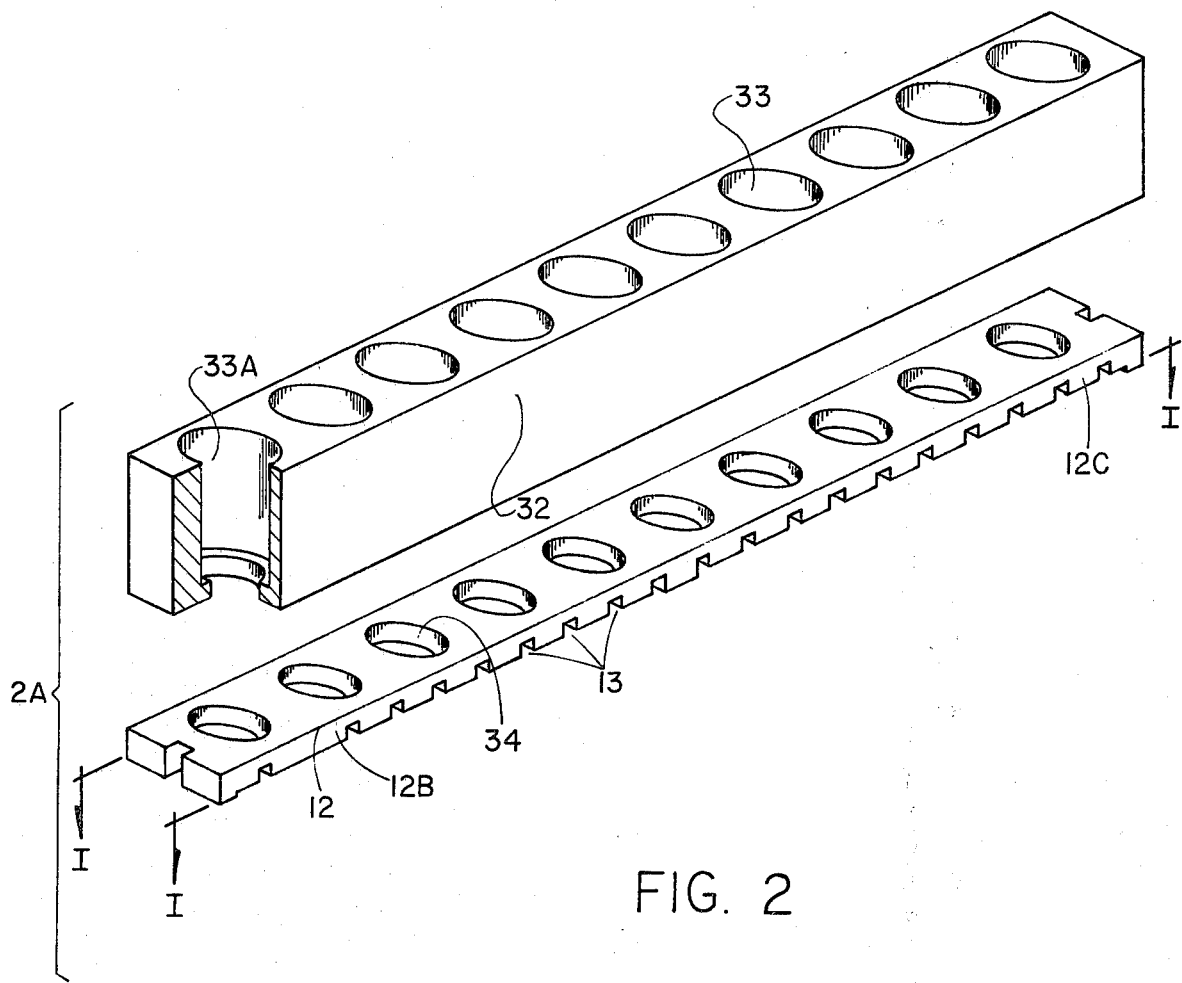
FIG. 2 shows an exploded view of a support for sample test tubes, for use in the device of FIG. 1.

As shown in FIG. 2, holders or supports 12A for sample containing test tubes consist of two parts, a lower-most tray carrier 12, and a tray 32 thereupon. Tray 32 is removably engaged on top of carrier 12 in registration with respect thereto by known expedients, such as short pins in one part and complimentary recesses in the other, which are known as such and have not been shown. Tray and carrier have substantially the same horizontal shape and dimensions, and are longitudinally elongated; in this embodiment tray 32 has but one row of ten test tube receiving locations. Bores 33 in tray 32 define receptacles adapted to support test tubes therein. The first of bores 33 has been shown broken away in part.

The carrier 12 preferably has circular holes 34 coaxial with the bores 33 and tray 32, to allow a pin to be passed upwards through the bore from below. Thus, for example, each test tube in turn may be lifted from its tray up to a sample processing station as the tray is passed thereby for sample preparation measuring, counting or other processing. As will be seen more clearly later, this subdivision of the sample support 12A into tray carrier and tray allows carriers 12 to be a permanent and integral part of the changer mechanism to be described. This in turn avoids the need for the machine to be operated with its full compliment of trays, thus providing improved convenience for the user. Although the tray carriers are integral parts of the changer mechanism, they nevertheless can be easily removed therefrom. The trays 32 are, of course, removable from the carriers, hold test tubes both in the machine and when placed elsewhere in the laboratory, and can be removably engaged interchangeably on any carrier 12 at will.

Over the lower surface of each tray carrier 12 are grooves or slots 13 extending transversely across the width of the carrier perpendicular to the longitudinal axis of the carrier, and opening downwardly. These grooves or slots 13 are of a height complimentary to the thickness of pins or projections 9 in the apparatus to be described, so as to allow such pins or projections 9 to enter into and along the grooves or slots and so engage the carrier 12. The slots are longitudinally spaced from each other by a given distance which bears a regular relationship to the spacing between the sample receiving bores. However, limited portions 12B and 12C of carriers 12 adjacent to each end thereof are not provided with slots, so that the last slot at each end of carrier 12 is spaced a greater distance from its neighbor than the other slots. The exact spacing relationship of the slots will be elaborated below.

Figure 1:
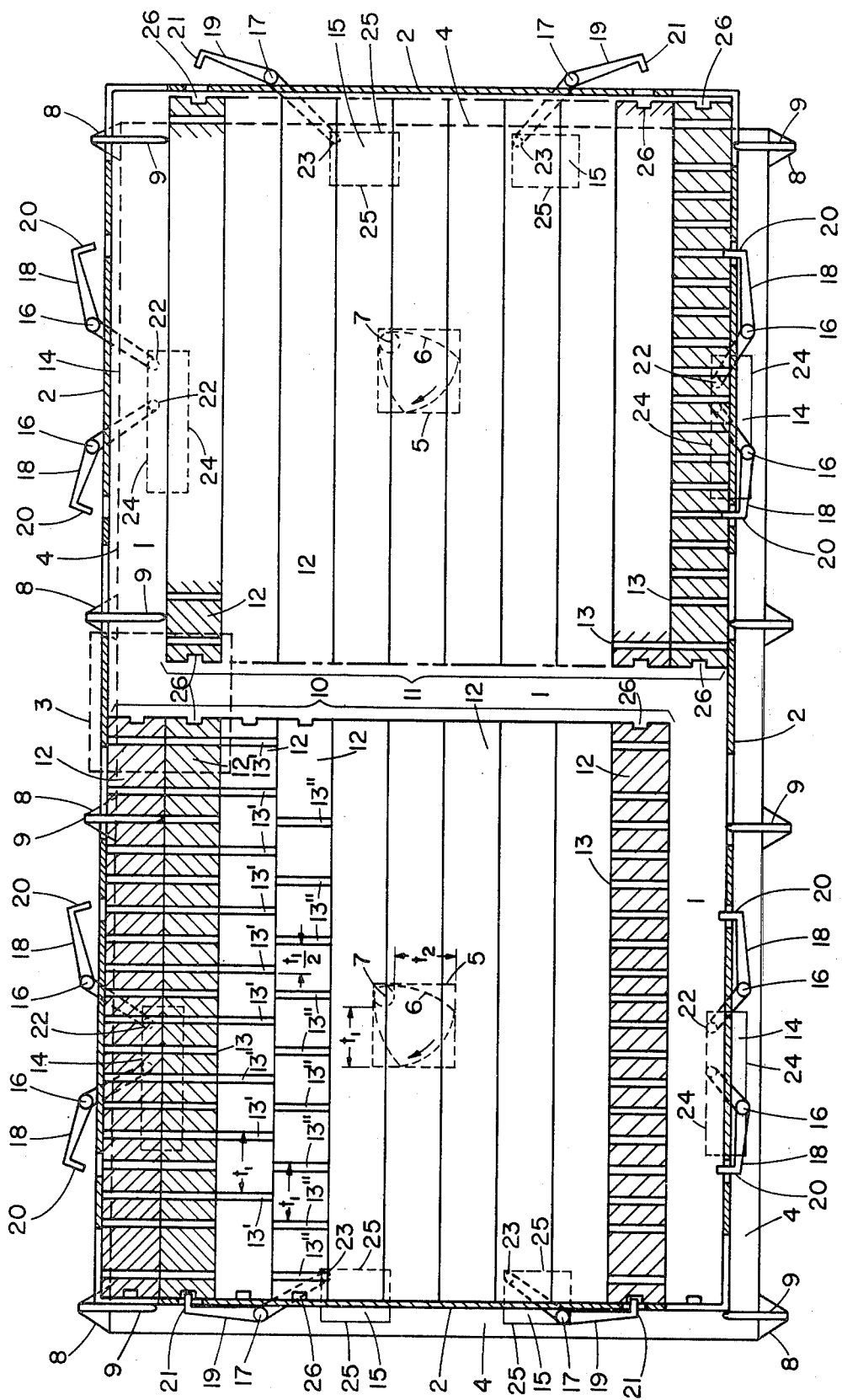
FIG. 1 is a top planar view of a mechanism according to the invention including a table with a plurality of elongated sample supports upon it, in which some supports are shown in horizontal sections through their lower portions.

In FIG. 1 the tray carriers 12 are shown in horizontal section along lines I—I in FIG. 2, but without the bores 34, which intersect the grooves 13 at regular intervals. The table 1 is of rectangular shape with upturned edges 2, which are shown in the same horizontal section as the horizontal section I—I. At the position indicated at 3, there may be a station for treating, measuring or counting etc. It will be seen that the paths of the carriers on table 1 is such that all the test tubes will be fed past this station, for treatment or measurement. For example, at station 3 the tubes can be sequentially taken from their holders, pushed therefrom to the treating or measuring station, and again returned into the holder from which originally removed. Such stations are known in many different embodiments, depending on the purpose, the shape of the test tubes, etc., and it will not be necessary to describe such a station in further detail, as such a station does not form a part of the present invention.

Below table 1 a rectangular horizontal plate 4 is provided having generally the same dimensions as the table. Plate 4 has one square opening 5 and one rectangular opening 5', into which are engaged cams 6 rotating about axes 7. These cams are powered continuously and are rotated normally in the direction of the arrows shown with the cams. The cam spindles on axis 7 are driven in the same direction, preferably from a common driving motor (not shown) below the table.

Plate 4 is further provided with eight protruding brackets 8, four along each longer side thereof at the upper and lower edges of the plate. Each such bracket carries a projection 9 held above table 1 by the brackets. The pins or projections 9 each are parallel to the other and point inwardly toward the table, and all the pins lie in a plane just above that of the table 1. Plate 4 may also have other openings (not shown) to allow the passage of stationary supports for the table, or a plunger means to move the test tube samples in and out of the trays at test station position 3. In any event, however, the table is supported and the sample transfer mechanism is such that the plate is not hindered in its ability to be moved relative to table 1 under the influence of the rotating cams 6.

Table 1 carries two rows of tray carriers 12, one row being indicated by 10 and the other by 11. In each row a number of supports or holders 12A are carried one adjacent the other, with the elongated side of one holder in contact with the elongated sides of the holders on either side thereof. In FIG. 2 a number of holders 12A are shown in section through their carrier portions 12, the section being taken in accordance with section I—I as in FIG. 2. Each row 10 and 11 carries ten tray carriers 12, with the table having space for eleven of such carriers 12, or complete holders 12A. Thus, one of the carriers at the opposite ends of each row is normally in the process of undergoing movement to the opposite row. It will be appreciated that the holders move in a rectangular path over the table with the trays in one row moving upwardly (as depicted in FIG. 1) while the trays in the other row are moved downwardly, and with trays at the diagonally opposite ends of each row being incrementally moved over to the opposite row in the longitudinal direction of the carrier.

To appreciate the mechanism which powers the travel of holders 12A, the basic relationship between the plate 4, the cams, and the relationship between the projections or pins 9 and the tray carriers must be understood. The plate 4 moves relative to table 1 in a rectangular path, which may be square, and is offset about table 1. With reference to FIG. 1, one phase of the movement along this path is from left to right, with a stroke $t_1$, and a second phase of the movement is from top toward bottom in the drawing with a stroke $t_2$; these strokes may, of course, be equal. This means that the projections 9 which are mounted upon plate 4 also move in such a rectangular square path, with a stroke $t_1$ from left to right (and from right to left) and with a stroke $t_2$ which may be equal to $t_1$, and which normally is equal to the width of one of the carriers 12, from top to bottom (and from bottom to top) of FIG. 1.

The slots 13 of carriers 12 are regularly spaced in a simple relationship to the stroke $t_1$. As seen, for example, from the upper two carriers 12 at the left top corner of FIG. 1, the slots 13 are not all equally spaced at the same mutual distance. As mentioned above, the two slots near the ends of the carriers are spaced by a larger mutual distance from the adjacent slots than in the central part of the carriers. This variant spacing, and its relationship to stroke $t_1$, have important implications for the operations by which the trays are moved.

To better understand the slotting pattern, the slots of each carrier may be thought of as being divided into two groups, in which in each group the slots have the same spacing therebetween, or the same mutual distances. The third and fourth carriers 12 from above in the left hand row 10 of FIG. 1 have been utilized to illustrate the concept, a set of alternate slots being left out of the illustrations for each of these two trays, with the omitted set differing in each. This third carrier illustrates one of the groups 13' of slots, and the fourth carrier illustrates the other slot group 13". The slots 13' begin near the right end of the third carrier, have mutual distances $t_1$ therebetween, but lack the last slot which could have been made at the left of the third carrier illustration. The second group begins near the left end of the fourth carrier and has the slots 13" also at mutual distances equal to $t_1$ therebetween, but lacks a slot near the right end of the fourth carrier illustration. The mutual distances between the two adjacent slots of both groups is, of course, one-half $t_1$. It will be understood that slot groups 13' and 13" in the illustrated third and fourth carriers are shown only for explaining the position of the slots, and that each carrier in actuality of course has both groups of slots.

Adjacent ones of projections 9 in each row of projections have mutual distances therebetween which are fixed at a distance which is not equal to a whole number times stroke $t_1$. Rather, in the illustrated embodiment, such distances are equivalent to a whole number times one-half $t_1$. In fact the two adjacent projections 9 to the left of the center of the length of table 1, and those two adjacent projections to the right thereof, have a distance therebetween which is $8\frac{1}{2}$ times $t_1$. The two adjacent projections 9 near the center of the length of table 1 have a mutual distance of $3\frac{1}{2}$ times $t_1$. The distance of $8\frac{1}{2}$ times $t_1$ is the same as the distance from the center of the part of carrier between the slots 13" at the outer left end of each carrier, where a slot 13' is lacking, to the center of the part of the carrier near the right end between adjacent slots 13', where a slot 13" is lacking.

The operation of this device may be described as follows. In the position of all parts as shown in FIG. 1, and with the cams 6 rotating in the direction of the arrows shown therein, the projections 9 are moved upwardly. The right one of the two projections 9 at the upper left leaves the one of slots 13 into which it was engaged. The two projections 9 at the upper right move upwardly to free the way for row 11 of the carriers to move upwardly. The two projections 9 at the bottom left of course also move upwardly, but do not engage a carrier. The two projections 9 at the bottom right are each just in front of the end parts of the carriers, where a slot from one of the aforementioned slot groups is lacking as described. Thus, these projections push the entire row 11 of carriers upwardly by the distance equivalent to stroke $t_2$, which here is equal to the width of one of carriers 12.

Upon completion of this phase of the rectangular cycle of movement, plate 4 with the projections 9 moves to the right relative to table 1 over the distance $t_1$, but the projections do not engage the carriers, which thus remain stationary.

At the end of this phase of the movement to the right, the projections 9 move downwardly, again over a stroke $t_2$. This causes two projections at the left top of FIG. 1 to push the entire row 10 of carriers 12 downwardly, by engaging the side of the carrier at the top left at the position where a slot from one of the slot groups is lacking as described above. At the right top end of FIG. 1, above row 11, the left one of the two projections 9 moves into a slot 13 of the adjacent carrier in row 11. The remaining ones of projections 9 do not engage any carriers.

At the end of the foregoing downward stroke, the projections 9 move to the left over a distance equal to stroke $t_1$, which causes the left projection 9 at the top right, which engages a slot, to move this top carrier of row 11 to the left by one incremental step equal to stroke $t_1$. In this embodiment the stroke $t_1$ is related to the spacing between adjacent test tube receptacles so that this movement causes the first test tube on the carrier to be positioned at measuring station position 3.

At the next upward movement of plate 4, the right one of the two projections at the bottom left engages a slot 13 in the lowermost carrier of row 10, and on the next movement of plate 4 to the right, this carrier is moved one incremental step equivalent to stroke $t_1$ to the right away from row 10 toward row 11.

As long as a carrier is in a position in between alignment with row 10 or 11, the projections 9 always find slots with which to engage when the lowermost row of projections moves upwardly, and when the uppermost row of projections moves downwardly. Thus, on each movement of the projections 9 to the right, a carrier at the lower end of the row 10 is moved one step forward stepwise to row 11; and on each movement of the projections 9 to the left, a carrier at the upper end of the row 11 is moved stepwise to row 10 along past station 3. There will thus be a test tube receptable or recess of a holder 12A stationary at station 3 once in every full rectangular movement of plate 4 with its projections 9. This test tube recess will remain stationary at station 3 during three of the four phases of the movement of projections 9 over their rectangular path. This means that rapid shifting of the test tubes to and from the station is possible notwithstanding a relatively long time interval out of the cycle of movement of plate 4 during which they reside at station 3.

In accordance with a further feature of the invention, plate 4 includes a number of rectangular openings, two near each of its long sides along the bottom and top margins, and indicated at 14, and two near each of the shorter sides along the side margins, and indicated at 15. Near each opening 14 there are two stationary pivots 16 just outside the table and above plate 4. Near each opening 15 there is one such pivot indicated as 17. The pivots 16 and 17 are vertical and carry two-armed levers 18 and 19 respectively. Each of these levers has at the ends of one of their arms the locking protrusions 20 and 21 respectively, and at the ends of their other arms the projections 22 and 23 respectively, the latter engaging the edges of the openings 14 and 15 respectively. The carriers all are provided with locking recesses 26 formed in the margins of each of their ends so as to allow the locking projections 21 to engage therein.

Plate 4 operates these locking parts at the end of each one of its strokes. The vertical movement or stroke operates levers 18, and the horizontal movement or stroke operates levers 19. During a vertical stroke, levers 18 engage opposite edges 24 of openings 14 by means of projections 22, while during a horizontal stroke, levers 19 engage opposite edges 25 of openings 15 by means of projections 23. Since edges 24 and 25 for each opening 14, 15 are rather far apart, they will leave levers 18 and 19 stationary over the greater part of the movement cycle of plate 4, and will only move them near the end of one of the strokes of plate 4. This leaves the locking parts in locking and unlocking positions as long as possible, to result in locking engagement during the longest possible period. By this locking system the locking means are only moved during a stroke of plate 4 which does not move a carrier in the direction which is influenced by such locking means. Thus, locking protrusions 21 are only moved by horizontal movements of plate 4; protrusions 21 do not impair horizontal movements of the holders, but rather only lock the system against vertical movements. Similarly, protrusions 20 do not affect vertical movements, but rather lock against horizontal movements. It will be appreciated that this arrangement thus provides a very simple and reliable locking system.

The carriers may be shorter than shown (or each group of slots 13 may terminate closer to the end of each carrier) so that the locking slot from one group is not followed by a terminal slot of the other group. In such a case, the left-hand slot 13" and the right-hand slot 13' may be omitted. Moreover, the two groups of slots need not be displaced by half the stroke $t_1$ in the direction perpendicular to the length of the slots. As each moving projection 9 only engages the slots of one group and not of the other group, the displacement of one group with respect to the other may have any desired value, for example, one-third or one-fourth of the stroke $t_1$ instead of half $t_1$ as shown in the figure. In such other cases, any slot 13" between two adjacent slots 13' will have unequal distances to such adjacent slots 13'. Preferably, the test tube recesses or receptacles are spaced a distance 2t₁; however, any other regular multiple of the $t_1$ stroke may be utilized also.

The carriers 12 may have rounded edges to avoid jamming when a carrier is moved from one row to the other of rows 10 and 11. The stroke $t_2$ may well be somewhat longer than $t_1$, and than the width of the carriers, in order to free the projections 9 in better fashion from the carriers without sliding in contact with them during stroke $t_1$. This does not complicate the drive because the foregoing result may be accomplished easily by making the openings 5 in the plate somewhat rectangular rather than square.

We claim:

1. In a conveying mechanism for stepwise movement of elongated carriers for test tubes to and away from a station for measuring or treatment, including a number of elongated carriers, each for receiving a plurality of said test tubes, a table on which a plurality of said carriers can be positioned in two parallel rows, with the longer sides of the carriers in each row along side each other, means for first moving the carriers at diagonally opposite ends of said rows oppositely in longitudinal directions stepwise from one row into the other row, and for secondly moving the carriers in each row in opposite directions transverse to said longitudinal directions, whereby said means for moving the carriers in a rectangular path over the table, the improvement which comprises: providing each of the carriers with a plurality of slots in their lower surfaces extending transversely to the longitudinal direction of the carriers; said means for moving the carriers in the longitudinal direction and perpendicularly thereto being comprised of a plurality of mutually rigidly connected projections, insertable into the slots of said carriers, said moving projections being provided in two linear rows, each row being parallel to the longitudinal direction of the carriers on the table, said rows being generally spaced by a distance equal to the length of each row of carriers on the table, less the width of a carrier; driving means for moving said projections in a rectangular path in two longitudinal strokes and two transverse strokes to engage the slot of one end carrier at the end of one row, move said carrier incrementally longitudinally toward the other row, the diagonally opposite other end carrier on said table being conveyed similarly, said slots being spaced relative to each other and said projections so that upon said end carriers being fully aligned with their new rows, said projections engage non-slotted portions of said end carriers and moves the same transversely to said longitudinal direction to thereby position subsequent carriers to repeat the cycle.

2. The mechanism of claim 1, in which the improvement further includes the spacing of said projection rows by a distance equal to the length of each row of carriers on said table, less the width of a carrier, augmented by said stroke of the projections in the longitudinal direction, and decreased by the width of a carrier.

3. The mechanism of claim 1 in which the improvement further includes said slots being provided in two groups which in part overlap each other, each group having slots at mutual spacings equal to a longitudinal stroke of the projections, one group of slots lacking one slot near one end of each carrier, and the other group of slots lacking one slot near the other end of each carrier.

4. The mechanism of claim 3, in which the improvement further includes at least four projections in each of said projection rows, of which adjacent projections in said projection row have mutual distances unequal to a full number of times a longitudinal stroke, the projections to each side of the center of each projection row having a mutual distance greater than that part of the length of the carriers along which said groups of slots overlap, but smaller than the length of the carrier, so that both projections together in one of their positions at the end of a longitudinal stroke are positioned adjacent opposite portions of the carriers wherein there are no slots.

5. The mechanism of the claim 4, in which the improvement further includes the two projections closest to the center of each projection row having a mutual distance differing from a whole number times the stroke of the projections in the longitudinal direction by a length equal to the distance between adjacent slots of said two slot groups.

6. The conveying mechanism of claim 5 in which the improvement further includes the mutual distance between adjacent slots of said slot groups being equal to half the stroke of said projections in the longitudinal direction.

7. The conveying mechanism of claim 1, in which the improvement further comprises first movable locking means along first sides of the table parallel to the sides along which the rows of projections are positioned, said first locking means being adapted to move into and out of said slots of the carriers, said locking means being mechanically connected to said driving means for moving said projections through said rectangular path.

8. The conveying mechanism of claim 7, in which the improvement further comprises second moveable locking means along the two other, second sides of the table, the carriers having recesses or the like at their shorter ends into which said locking means engage.

9. The conveying mechanism of claim 1, in which the improvement further includes the driving means for the projections being comprised of a rectangular body below the table driven to move in said rectangular path of said moving projections, and to which body said projections are rigidly secured by upstanding bridge portions outside the table and connecting said rectangular body below the table to said projections above the table.

10. The conveying mechanism of claim 9, in which the improvement further includes first moveable locking protrusions along the sides of the table adapted to move into and out of recesses in said carriers to lock said carriers, said protrusions each being mounted on one arm of a lever with a stationary fulcrum, said lever having another lever arm cooperating with cam means for reciprocating the lever between a locking and an unlocking position of its locking protrusions, said rectangular body carrying said cam means for reciprocating the levers of the locking protrusions.

11. The conveying mechanism of claim 10 in which the improvement further includes said cam means being constituted by the edges of openings defined in said rectangular body, into which openings said lever projections extend, each connecting to one of said other lever arms of the locking protrusions, said openings each having two opposite parallel edges cooperating with said projections on said levers, so that said levers are moved by the rectangular body during its stroke in one direction and are stationary during the stroke of said body in the direction perpendicular thereto.

12. The conveying mechanism of claim 11 in which the improvement further includes said parallel edges having a mutual distance greater than the dimension of the said lever projections so as to leave said lever projections extending into said openings and thus said lever arms and said locking protrusions stationary over the greater part of the stroke of the rectangular body in a direction perpendicular to said parallel edges and to move said lever projections and locking protrusions only near the end of said stroke of the rectangular body in said direction.

13. The conveying mechanism of claim 9, in which the improvement further comprises said rectangular body being comprised of a plate of generally similar dimensions to said table, said plate being provided with at least one generally rectangular opening, while the dimensions of said opening being related to said longitudinal and transverse strokes of said rectangular path, said driving means being further comprised of a cam engaged within said rectangular opening, whereby said plate and projections are driving to undergo motion in said rectangular path.

14. The conveying mechanism of claim 13, in which the improvement further comprises said generally rectangular opening being approximately square, and said cam being three-sided and engaging the edges of said rectangular opening with one side having the form of an arc of a circle.

15. The conveying mechanism of claim 13, in which the improvement further comprises a second generally rectangular opening defined within said plate, with a second driving cam engaged therein for better stability.

16. A transport mechanism for conveying samples to and from a test station, comprising:
a plurality of longitudinally elongated test tubes supports, each having a plurality of longitudinally evenly spaced receptables accepting test samples and having defined therebelow a plurality of longitudinally spaced grooves perpendicular to said longitudinal direction, and bearing a regular relationship with the spacing between said receptacles, said supports having a limited portion near the ends thereof which is not grooved;
a planar table mounting said supports in two side-by-side rows, with the longitudinal sides of the supports in each row positioned alongside each other, said table permitting said supports to be moved in a rectangular path, and longitudinally across as the ends of said rows into the opposite row;
a plate generally coextensive with and immediately underlying said table, and moveable with respect thereto, said plate having marginally mounted pins held above the margin of said table and extending parallel to, and in the plane, of said grooves, at least one such pin being provided at the ends of each of said rows, said plate being provided with at least one generally rectangular opening, the dimensions of said opening being related to the spacing between said grooves and the width of said supports; and
a cam engaging said opening for rotation therewithin to move said plate in a generally rectangular path off-set about said table and in a plane parallel thereto,
whereby said pins normally engage two sample supports positioned at the diagonally opposite ends of said two rows and move said two supports longitudinally across toward the opposite row by the incremental distance related to the spacing between two adjacent receptacles, this movement being repeated in sequence until each of said two supports align with the opposite row, whereupon the said pins engage said non-grooved portions of said supports and thereupon move said supports in the direction of said rows transversely to said longitudinal direction, to position subsequent supports at said diagonally opposite ends to repeat the cycle.

* * * * *